United States Patent
Hipps

[19]
[11] Patent Number: 6,162,208
[45] Date of Patent: Dec. 19, 2000

[54] ARTICULATING ENDOSCOPIC IMPLANT ROTATOR SURGICAL APPARATUS AND METHOD FOR USING SAME

[75] Inventor: W. Michael Hipps, Augusta, Ga.

[73] Assignee: Genzyme Corporation, Cambridge, Mass.

[21] Appl. No.: 09/152,215

[22] Filed: Sep. 11, 1998

Related U.S. Application Data

[60] Provisional application No. 60/058,491, Sep. 11, 1997.

[51] Int. Cl.[7] .................................................. A61B 17/00
[52] U.S. Cl. .............................. 606/1; 623/2.11; 128/899
[58] Field of Search .............................. 606/1, 108, 170, 606/191, 205, 211; 623/2.11, 900; 249/24; 604/164, 183; 128/898, 899

[56] References Cited

U.S. PATENT DOCUMENTS

| | | |
|---|---|---|
| 2,079,233 | 5/1937 | Wappler . |
| 3,190,286 | 6/1965 | Stokes . |
| 3,799,151 | 3/1974 | Fakaumi et al. . |
| 4,483,562 | 11/1984 | Schoolman . |
| 4,754,909 | 7/1988 | Barker et al. . |
| 4,950,273 | 8/1990 | Briggs . |
| 4,982,727 | 1/1991 | Sato . |
| 5,035,248 | 7/1991 | Zinnecker . |
| 5,071,420 | 12/1991 | Paulos et al. . |
| 5,152,779 | 10/1992 | Sanagi . |
| 5,334,185 | 8/1994 | Giesy et al. . |
| 5,383,852 | 1/1995 | Stevens-Wright . |
| 5,467,763 | 11/1995 | McMahon et al. . |
| 5,520,696 | 5/1996 | Wenstrom, Jr. . |
| 5,540,706 | 7/1996 | Aust et al. . |
| 5,582,607 | 12/1996 | Lackman ...................................... 606/1 |
| 5,656,011 | 8/1997 | Uihlein et al. . |
| 5,776,187 | 7/1998 | Krueger et al. .......................... 623/2.11 |
| 5,788,689 | 8/1998 | Allan et al. ............................. 623/2.11 |

Primary Examiner—Linda C. M. Dvorak
Assistant Examiner—Bryan K. Yarnell
Attorney, Agent, or Firm—Richard D. Allison; Thomas J. DesRosier

[57] ABSTRACT

A surgical instrument is provided for use in endoscopic and open surgical procedures, e.g., prosthetic implant replacement surgery. The instrument includes a handle portion, an endoscopic tube section extending from the handle portion, an articulating section pivotally connected to a distal end of the tube section, and an implant adaptor operatively associated with the articulating section. Structure is provided for progressively manipulating the articulating section of the instrument relative to the longitudinal axis of the handle portion within an angular range of motion. Structure is further provided for rotationally manipulating the implant adaptor relative to the extended longitudinal axis of the distal end of the articulating portion.

33 Claims, 4 Drawing Sheets

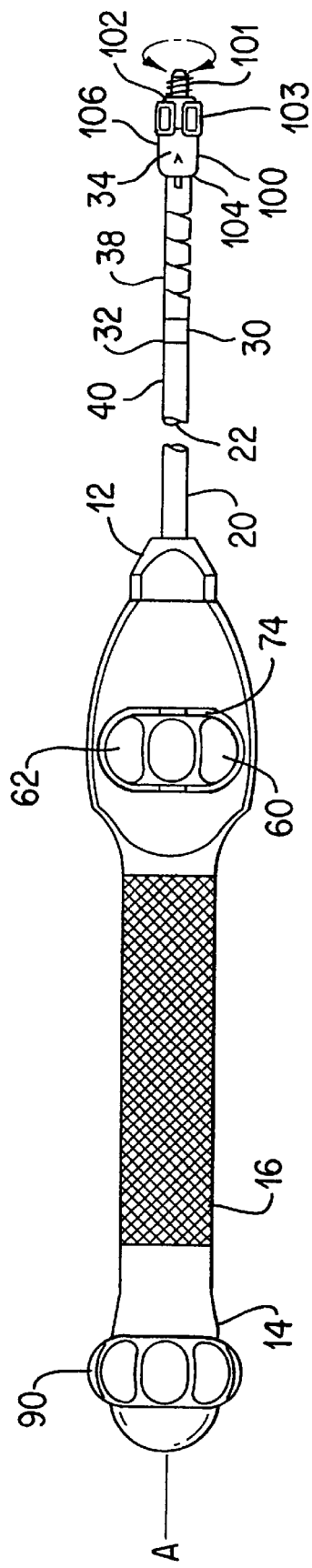
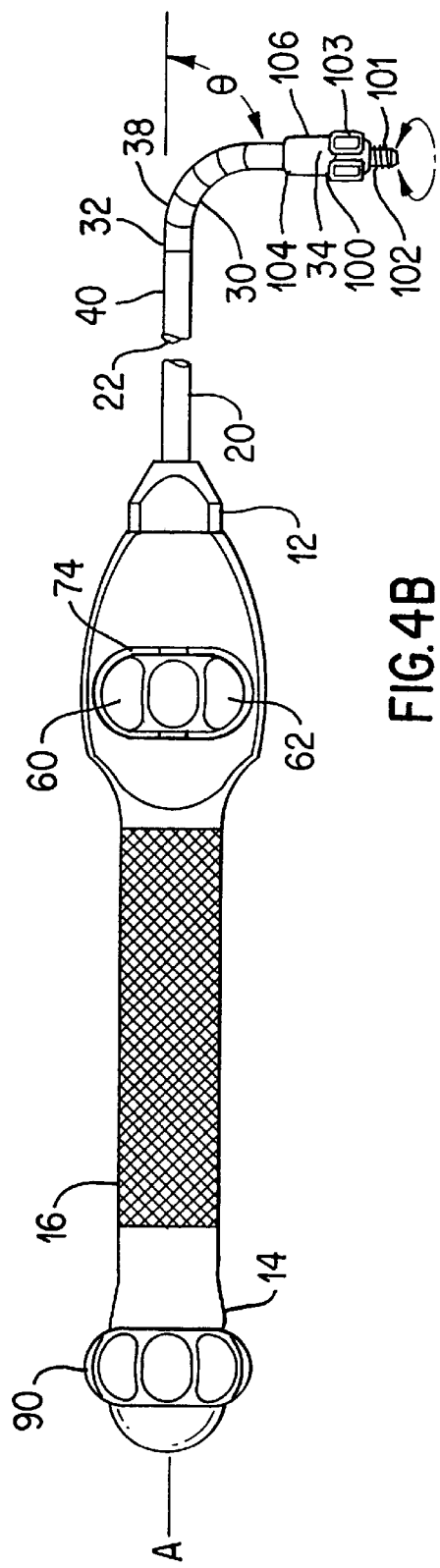
FIG. 4A
FIG. 4B

ARTICULATING ENDOSCOPIC IMPLANT ROTATOR SURGICAL APPARATUS AND METHOD FOR USING SAME

This application claims priority to Provisional Application Ser. No. 60/058,491, which was filed on Sep. 11, 1997.

BACKGROUND OF THE INVENTION

1. Field of the Invention

The subject invention relates to surgical instrument for performing endoscopic and open surgical procedures, and more particularly to surgical instrument having an end portion which can articulate a prosthetic implant, such as a heart valve, in a patient's body during a surgical procedure.

2. Background Art

In endoscopic surgery it is often advantageous to be able to precisely orient a prosthetic implant in a surgical site within the patient's body. One example in which it is critical to properly orient a prosthetic implant is in the medical field of open heart surgery and particularly in the field of prosthetic heart valve implantation. Open heart surgery, especially aortic and mitral valve replacement surgery, requires specialized tools adapted for these highly technical and precise procedures. In prosthetic heart valve implantation, for example, specially adapted instruments for handling the prosthetic valve include valve sizers, valve rotators, leaflet testers, and handles for the rotators. Many of the instruments needed for prosthetic valve replacement surgery are sold in kits, e.g., such as those manufactured by CARBOMED-ICS® of Austin, Tex.

In a typical valve replacement procedure the surgeon will utilize a valve sizer to determine the proper size prosthetic replacement valve for the patient. The prosthetic valve is mounted on a valve holder and handle assembly and delivered to the surgical site. Often times it is necessary to rotate the valve to obtain the best orientation with respect to the location of the patients remnant valve leaflets and chordae tendinea. Improper orientation of the prosthetic valve will cause impaired function of the synthetic leaflets due to interference with one or more of the above structures. Thus, the surgeon places the valve into position with one instrument and then must utilize another separate instrument for rotation and anatomical orientation of the leaflets.

Recent advances in prosthetic heart valve implantation include the advent of newer minimally invasive and endoscopic surgical approaches. These new surgical procedures are less stressful on the coronary care patient and reduce patient recovery times as well as increasing the success of the overall surgical procedure. However, the reduced surgical field makes positioning and orientation of the valves even more difficult and tedious.

Prior to the present invention, however, there was not a single instrument which was adapted for conventional as well as minimally invasive or endoscopic prosthetic implantation surgery, such as endoscopic valve replacement surgery, which could be used to hold a prosthetic implant for placement at the surgical site and also simultaneously be utilized to rotate the prosthetic implant into proper anatomical orientation.

SUMMARY OF THE INVENTION

The above problems of the prior art are overcome by the endoscopic surgical instrument of the present invention for use in positioning and placement of a prosthetic implant during surgical procedures performed within a patient's body and particularly within the thoracic cavity. This surgical instrument is ideally suited for positioning and placement of a prosthetic heart valve in open, non-endoscopic, or minimally invasive surgical procedures performed within the thoracic cavity.

The surgical instrument of the subject invention includes a handle section having a handle section, an endoscopic portion which depends from the handle section and a tool adaptor freely rotatably about the distal end of the endoscopic portion. The endoscopic portion includes an elongated rigid tube section and a tubular articulating section which is pivotally connected adjacent to the distal end of the endoscopic portion.

Bending structure is associated with the articulating section of the instrument for selectively pivoting the articulating section in an angular plane passing through the longitudinal axis of the handle section within a desired angular range of rotation. This bending structure is preferably controllable from the handle section of the instrument which is preferably exterior to the patient's body when the instrument is in use. One preferred embodiment includes an articulating section with a desired angular range of rotation of about 0 to 90°.

The articulating section preferably includes pivotally interengaging segments having substantially the same diameter and internal bore as the endoscopic section. Each segment, when pivotally connected to either the rigid section or another segment, allows for the rotation of the articulating section within an angle of rotation. The desired maximum articulating section angular range of rotation may be selected by the selective addition or deletion of links which would have the desired result of increasing or decreasing, respectively, the desired angular range of motion.

The bending structure for pivoting the articulating section of the endoscopic section preferably may include a flexible member, which preferably is a metal wire, extending from near the distal end of the articulating section to a tensioning mechanism and passing within the rigid tube and articulating sections. The axial translation of the flexible member caused by the operation of the tensioning mechanism induces tension into the flexible member and forces the articulating section to pivot within the desired angular range of rotation relative to the longitudinal axis of the handle of the instrument.

The tensioning mechanism may comprise a lever connected to the flexible member and axially movable between a plurality of positions so that the articulating section may be selectively positioned.

The tensioning mechanism may comprise a screw member longitudinally disposed within the body of the handle. The screw member is arranged to cause translational movement in an axial direction in response to rotation of an axially threaded actuation nut that is threadably connected to the screw member. Rotation of the threaded knob would cause the screw member to translate axially, which in turn would cause the attached flexible member to translate coaxially, thereby tensioning the flexible member and causing the articulating section to pivot within the desired angular range of rotation relative to the longitudinal axis of the handle section of the instrument.

A implant adaptor, freely rotatable about the distal end of the articulating section, is associated with a rotation structure for selectively rotating the tool adaptor relative to the extended longitudinal axis of the distal end of the articulation section. There are no angular limitations to the rotation of the tool adaptor assembly by the rotation structure. The rotation of the tool adaptor is preferably controllable from the handle section of the instrument which is preferably exterior to the patient's body when the instrument is in use.

The rotation structure for the implant adaptor may include a rod member extending through the handle and the bores of the rigid tube and articulating sections to the distal end of the articulating section. The implant adaptor would be fixed to the forward end of the rod member and would preferably have a internal bore in the bottom end of the implant adaptor with an inside diameter and depth sufficiently large enough to allow the implant adaptor to be seated onto the distal end of the articulating section while providing for non-binding rotation of the implant adaptor about the distal end of the articulating section. The proximal end of the rod member would be secured to a rotation knob disposed adjacent the handle section. The length of the rod member would be sized to ensure that the implant adaptor assembly would remain seated about the distal end of the articulating section. Rotation of the rotation knob would cause the rod member to angularly rotate, thereby causing the implant adaptor to correspondingly angularly rotate.

The rod member is preferably made of a flexible metal that has an inherent metal memory for allowing the recovery of its initial, substantially linear shape, after being bent. This would allow the rod member to necessarily bend in response to the pivoting of the articulating section relative to the longitudinal axis of the handle. The inherent metal memory of the flexible rod member would also provide a spring force for reducing the effected angular range of rotation of the articulating section as tension on the flexible member is released through rotation of the actuation nut. One preferred embodiment would include a rod member made up of a length of a flexible memory metal connected to a length of a non-flexible metal. This would allow for the length of the flexible memory metal portion of the rod member to be positioned toward the forward end of the rod member proximate and within the articulating section of the instrument thereby providing flexibility and spring force where desired.

The combination of the flexible metal wire and the flexible memory metal rod member allows for the precise pivotal positioning of the distal end of the articulating section. A gradual manipulation of the actuation nut allows the distal end of the articulation section to be put in tension and causes the distal end of the articulation section to pivoted from the longitudinal axis of the endoscopic section at a controlled rate to a desired operative position. As the articulation section is pivotally rotated, the flexible memory metal rod member is placed under a bending load which acts to attempt to return the articulating section to its original position, co-axial with the endoscopic section, when the actuation nut is manipulated in the opposite direction.

Further features of the subject invention will become more readily apparent from the following detailed description of the invention taken in conjunction with accompanying drawings.

BRIEF DESCRIPTION OF THE DRAWINGS

Preferred embodiments of the subject invention will be described herein with reference to the drawings wherein:

FIG. 4A is a plan view of the articulating endoscopic surgical instrument showing the articulating section in a fully-extended position co-axial to the longitudinal axis of the handle; and, FIG. 4B is a plan view of the articulating endoscopic surgical instrument showing the position of the instrument when the articulating section is selectively deflected in an angular plane passing through the longitudinal axis of the handle within a desired angular range of motion.

DETAILED DESCRIPTION OF THE PREFERRED EMBODIMENT

Figure 1:
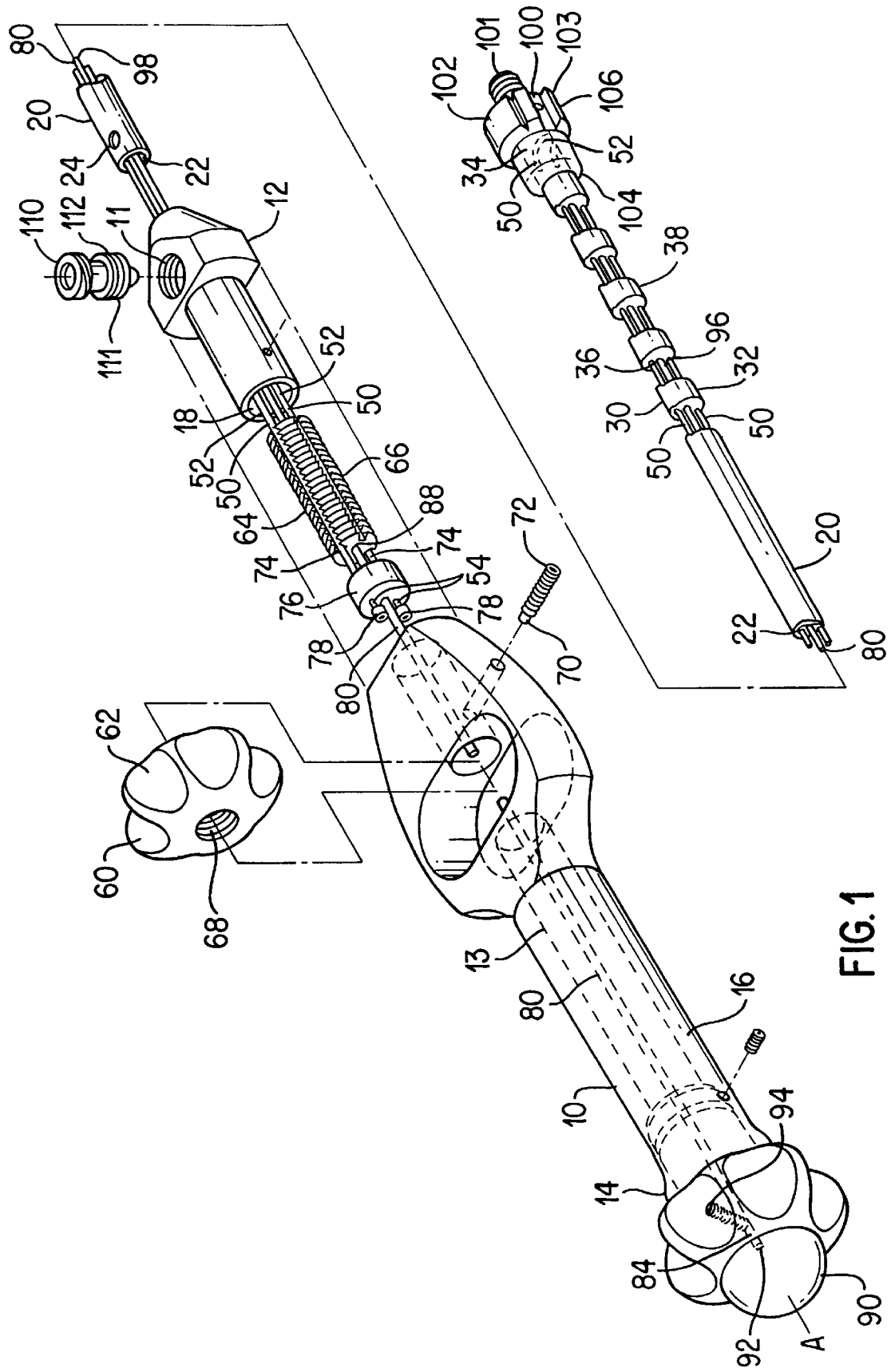
FIG. 1 is an exploded view of an articulating endoscopic surgical instrument in accordance with the preferred embodiment of the present invention.

The present invention is more particularly described in the following examples which are intended as illustrative only since numerous modifications and variations wherein will be apparent to those skilled in the art. As used in the specification and in the claims, "a" can mean one or more, depending on the context in which it is used.

The present invention, as shown in FIGS. 1–4B, encompasses a surgical instrument 5 for articulating a prosthetic implant during surgical procedures performed within a patient's body so that the prosthetic implant may be held in a desired position and rotated into proper anatomical orientation to enable the surgical implantation of the implant. The surgical instrument 5 of the present invention comprises an elongated handle 10, an elongated rigid tube section 20, an elongated tubular articulating section 30, a bending means for effecting pivotal movement of the articulating section 30, an implant adaptor 100, and a rotation means for effecting rotational movement of the implant adaptor 100. It is preferred that the handle 10, the tube section 20, the articulating section 30 and the implant adaptor 100 be constructed of stainless steel or other acceptable material for surgical instruments.

It can be appreciated by one skilled in the art that the instrument 5 of the present invention can be utilized at any location on or within the body where implantation of a prosthetic implant device is desired. As set forth in greater detail below, the unique design of the instrument 5 also provides the added feature of using the instrument 5 of the present invention to capture and remove previously implanted prosthetic implants.

The handle 10 is used to extend the rigid tube section 20 and the articulating section 30, forming an endoscopic portion 40, into the body cavity of the patient to reach a surgical site. The handle 10 has a front end 12, an opposite rear end 14, and defines a longitudinal axis A. As shown in FIG. 1, the handle 10 preferably has a hand grip 16 disposed near its rear end 14.

Still referring to FIG. 1, the rigid tube section 20 is connected to the front end 12 of the handle 10 and extends longitudinally from the front end 12. The rigid tube section 20 defines a tube bore 22 that extends therethrough the length of the tube section 20. The rigid tube section 20 is used to minimize the required length of the articulating section 30 as the endoscopic portion 40 is inserted into the patient's body cavity. Minimizing the length of the articulating section 30 aids in stabilizing the implant adaptor 100 when the implant is brought into, and held in, the desired position within the surgical site.

The articulating section 30 has a proximal end 32, an opposite distal end 34 and an articulating bore 36 that extends therethrough the articulating section 30. The proximal end 32 of the articulating section 30 may be pivotally connected to the rigid tube section 20. It is preferred that the articulating section 30 rotates in an angular plane passing through the longitudinal axis A of the handle 10 to aid in orienting the implant releasably secured to the implant holder. As shown in FIGS. 1, 4A and 4B, the articulating section 30 preferably comprises a plurality of interengaging segments 38 that are co-axially aligned with each other and that are pivotally moveable relative to each other. The segments 38 preferably have the same diameter and bore dimension as the rigid tube section 20 to provide ease of insertion of the endoscopic portion 40 into the body cavity during minimally invasive surgery and to minimize binding and obstruction with other instruments or adjoining tissues when the segments 38 are in the surgical field.

Each segment 38, when pivotally connected to either the tube section 20 or another segment 38, allows for the rotation of the articulating section 30, relative to the longitudinal axis A of the handle 10, within an acute angle of rotation defined by an angular gap 42 existing between the segments 38. The desired maximum angular range of motion Θ of the articulating section 30 may be selected by the selective addition or deletion of segments 38 which would allow for the increase or decrease, respectively, of the desired angular range of motion Θ of the articulating section 30. It is preferred that the desired angular range of motion Θ is between 0° and 90°. As one skilled in the art will appreciate, any configuration for the structure of the articulating section 30 can be utilized so long as the articulating section 30 can be selectively articulated within the desired angular range of motion Θ within the same angular plane passing through the longitudinal axis A of the handle 10.

Figure 2:
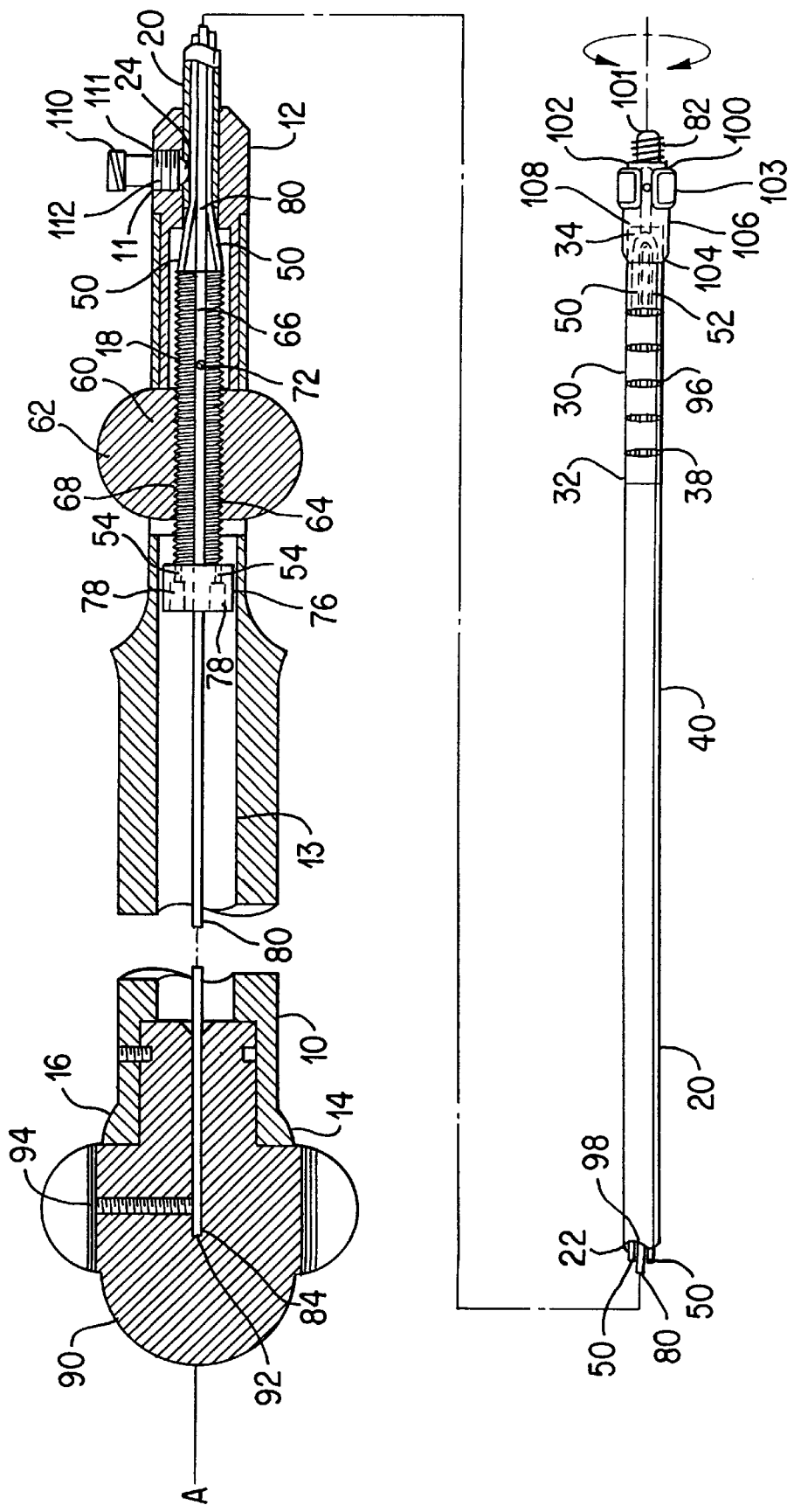
FIG. 2 is a partial sectional view of the articulating endoscopic surgical instrument showing the articulating section in a fully-extended position co-axial to the longitudinal axis of the handle.
Figure 3:
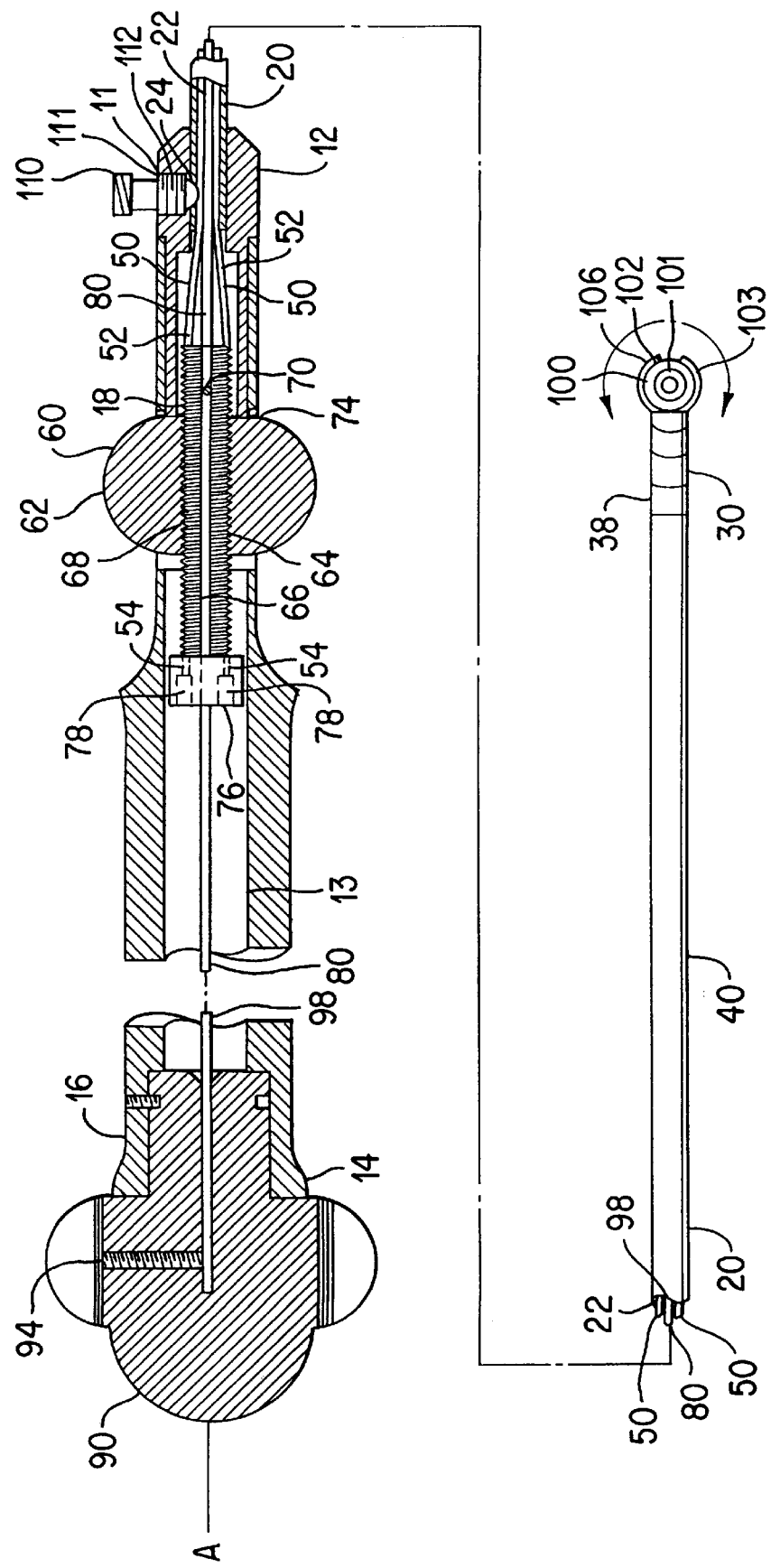
FIG. 3 is a perspective view of the articulating endoscopic surgical instrument showing the position of the instrument when the articulating section is selectively deflected in an angular plane passing through the longitudinal axis of the handle within a desired angular range of motion.

Another aspect of the present invention is that the instrument 5 further comprises a means for effecting pivotal, or bending, movement of the articulating section 30 by selectively deflecting the articulating section 30 from a fully-extended position to a plurality of operative positions. As shown in FIGS. 2 and 4A, the articulating section 30 is co-axial to the longitudinal axis of the handle 10 when the articulating section 30 is fully-extended. However, as shown in FIGS. 3 and 4B, when the articulating section 30 is selectively deflected, the articulating section 30 bends in the angular plane passing through the longitudinal axis A of the handle 10 within the desired angular range of motion Θ. The articulating section 30 may be selectively positioned at a plurality of operative positions withing the desired angular range of motion Θ.

In the preferred embodiment, the bending means comprises a flexible member 50 and a tensioning mechanism 60. Referring back to FIG., the flexible member 50 extends within articulating bore 36 of the articulation section and the tube bore 22 of the rigid tube section 20 and is connected near the distal end 34 of the articulating section 30 and is also operatively connected to the tensioning mechanism 60. The axial movement of the flexible member 50 caused by the application of tension to the flexible member 50 upon the operation of the tensioning mechanism 60 is transmitted to the portion of the flexible member 50 connected to the distal end 34 of the articulating section 30, thereby permitting the entire length of the controllably bendable articulating section 30 to be selectively deflected in the angular plane passing through the longitudinal axis A of the handle 10.

The flexible member 50 is preferably a non-stretchable wire. It is also preferred that the flexible member 50 comprise a plurality of wires so that the articulating section 30 may be smoothly brought into the selected operative position within the surgical site and then held in position without undesired movement of the articulating section 30 when in the operative position. A single flexible member 50 could be used in the present invention, but it is less desirable because it would likely be less stable in the operative position.

As shown in FIG. 1, the preferred embodiment of the flexible member 50 is a loop of wire 52 operatively connected at its free ends 54 to the tensioning mechanism 60 and connected near the distal end 34 of the articulating section 30. In this embodiment, the loop of wire 52 extends from the tensioning mechanism 60 through the tube bore 22 and the articulating bore 36 to near the distal end 34 of the articulating section 30 and thence returning to the tensioning mechanism 60 via the tube bore 22 and the articulating bore 36. This embodiment provides the stability advantages desired for the articulating section 30 by providing two lengths of wire extending within the articulating section 30 and the rigid tube section 20 while simplifying the construction of the surgical instrument.

In the preferred embodiment, the tensioning mechanism 60 comprises an actuation nut 62 and a longitudinally extending elongated threaded screw member 64. The actuation nut 62 is preferably mounted relative to the longitudinal axis A of the handle 10 and preferably is disposed within the body of the handle 10. It is also preferred that the actuation nut 62 be mounted toward the front end 12 of the handle 10 to allow for ease of use by the index finger or thumb of the surgeon as the handle 10 is grasped in the surgeon's hand. The actuation nut 62 has a threaded axial bore 68 extending therethrough the nut which is threadably associated with the threaded screw member 64. The screw member 64 is preferably oriented along the longitudinal axis A of the handle 10 so that when the nut is rotated in a clockwise direction, looking from the rear end 14 of the handle 10, the screw member 64 is caused to move translationally away from the front end 12 of the handle 10 in an axial direction relative to the longitudinal axis of the handle 10. This axial movement of the screw member 64 would cause the connected flexible member 50 to translate co-axially, thereby tensioning the flexible member 50 and causing the articulating section 30 to controllably deflect within the desired angular range of motion Θ.

The screw member 64 preferably moves translationally within a longitudinally extending sleeve bore 18 within the front end 12 of the handle 10 so that axial translation of the connected flexible member 50 is assured when the actuation nut 62 is operated. To ensure that the screw member 64 does not rotate as the actuation nut 62 is operated, the screw member 64 also preferably has an anti-rotation groove 66 in the exterior surface of the screw member 64 extending parallel to the longitudinal axis A of the handle 10. This anti-rotation groove 66 is in receipt of a complementary key 70 that extends into the anti-rotation groove 66 to prohibit rotation of the screw member 64 as it moves translationally within the sleeve bore 18 . The key 70 may be integrally formed into the sleeve bore 18 (not shown) or, preferably, as shown in FIG. 1, the key 70 may be formed by a set screw 72 extending from the surface of the handle 10, through the sleeve bore 18 and into non-binding orientation with the anti-rotation groove 66.

Other tensioning mechanisms 60 for providing a means for bending are contemplated including, for example, a lever 68 (not shown) or trigger mechanism in which the operation of the lever 68 causes the desired axial translation of the connected flexible member 50 and the controlled deflection of the articulating section 30. It is preferred that the lever 68 be axially moveable between a plurality of positions so that the articulating section 30 may be selectively positioned. However, this contemplated embodiment is less desirable because it would be difficult to hold the articulating section 30 in the desired position without the use of a clutch or holding mechanism. Such a clutch mechanism would make it difficult to selectively deflect the articulating section 30 to any desired operative position within the desired angular range of motion Θ as it would be contemplated that such a clutch mechanism would use discrete settings in which the articulating section 30 could be rotated.

The flexible member 50 may be attached to the portion of the screw member 64 that is oriented toward the front end 12 of the handle 10 by mechanical or chemical means that are common to one skilled in the art. Alternatively, as shown in FIG. 1, the screw member 64 may have a plurality of axial grooves 74 extending the length of the screw member 64 of a sufficient depth to accept the flexible member 50 within the axial grooves 74 without causing binding of the actuation nut 62 as it is rotated about the screw member 64. These axial grooves 74 extend parallel to the longitudinal axis A of the handle 10. In this embodiment, if the preferred embodiment of the flexible member 50 is used, i.e., the loop of wire 52, the free ends 54 of the loop are accepted within two axial grooves 74 of the screw member 64, that are preferably located on opposite sides of the screw member 64, and are mounted to a cap member 76 that is mounted onto the portion of the screw member 64 that is oriented toward the rear end 14 of the handle 10. The free ends 54 of the loop of wire 52 may be mounted by the attachment of cable swage collars 78 to the free ends 54 of the cable or by other mechanical or chemical means common to one skilled in the art.

Referring now to FIGS. 1–4B, the implant adaptor 100 of the present invention has a top end 102, a bottom end 104, and an exterior surface 106 that is shaped to removably engage a complementarily surfaced implant. The implant adaptor 100 is positioned next to the distal end 34 of the articulating section 30 and is freely rotatable about the distal end 34 of the articulating section 30. Preferably the bottom end 104 of the implant adaptor 100 defines an internal bore 108 with an inside diameter sized to freely overlap the outer surface of the articulating section 30 so that the implant adaptor 100 may be seated onto the distal end 34 of the articulating section 30. This preferred embodiment aids in preventing any undesired motion of the implant adaptor 100, other than the desired rotation of the implant adaptor 100 about the distal end 34 of the articulating section 30, which helps to hold the implant in place within the surgical field as the implant adaptor 100 is being oriented.

It is preferred that the implant adaptor 100 have the capability to removably engage any contemplated implant. To accommodate implants that have a female threaded engagement surface, it is preferred that the implant adaptor 100 have a male threaded post 101 that extends longitudinally from the top end 102 of the implant adaptor 100. The threaded post 101 is adapted to removably engage the implant's complementary female threaded surface. Similarly, to accommodate implants that have a female bayonet engagement surface, it is preferred that the exterior surface 106 of the implant adaptor 100 define a male bayonet fitting 103 that extends from the exterior surface 106 of the implant adaptor 100. The male bayonet fitting 103 is adapted to removably engage the implant's complementary female bayonet engagement surface. As shown in FIG. 1, it is preferred that the exterior surface 106 of the implant adaptor 100 have both the male threaded post 101 and the male bayonet fitting 103 so that the implant adaptor 100 may be accommodate more implant's without requiring the removal and change of the implant adaptor 100.

Another aspect of the present invention is that the instrument 5 further has a means for effecting rotational movement of the implant adaptor 100 about the distal end 34 of the articulating section 30 so that the implant adaptor 100 may be oriented relative to the distal end 34 when the distal end 34 is positioned and held in position. Referring to FIGS. 1–4B, the preferred embodiment of the rotation means comprises an elongated rod member 80 and a rotation knob 90. The rod member 80 has a forward end 82 and an opposed back end 84. The forward end 82 of the rod member 80 is fixedly connected to the bottom end 104 of the implant adaptor 100 so that rotation of the rod member 80 causes a corresponding rotational translation of the implant adaptor 100. The rod member 80 extends within the articulating bore 36 of the articulating section 30 and the tube bore 22 of the rigid tube section 20, and may extend into and possibly through the handle 10.

The rotation knob 90 is preferably mounted co-axial to the longitudinal axis A of the handle 10 and may be disposed within the body of the handle 10. The rotation knob 90 is operatively attached to the back end 84 of the rod member 80 so that the rod member 80 may be selectively rotated upon the rotation of the rotation knob 90 which causes the corresponding rotational movement of the attached implant adaptor 100 relative to the distal end 34 of the articulating section 30.

The rotation knob 90 preferably has an axial bore 92 extending at least partially therethrough for operatively receiving the back end 84 of the rod member 80. Preferably, the rotation knob 90 is secured to the rod member 80 by a set screw 94 extending through the rotation knob 90 and frictionally engaging a portion of the rod member 80. Removal of the set screw 94 allows for the removal and replacement of the rod member 80 and the connected implant adaptor 100 if desired. It is also preferred that the length of the rod member 80 be sized so that the implant adaptor 100 is retained on the distal end 34 of the articulating section 30, and still freely rotatable about the distal end 34, when the back end 84 of the rod member 80 is secured to the rotation member.

The rotation knob 90 may be mounted toward the front end 12 of the handle 10. However, as shown in FIG. 1, it is preferred that the rotation knob 90 be mounted toward the rear end 14 of the handle 10 to allow for ease of orientation of the implant via the implant adaptor 100 by the surgeon. When viewed axially, if the rotation knob 90 is mounted toward the rear end 14 of the handle 10, the rod member 80 extends from the bottom end 104 of the implant adaptor 100, within the articulating bore 36 of the articulating section 30, within the tube bore 22 of the rigid tube section 20, within a handle bore 13 that extends from the front end 12 to the rear end 14 of the handle 10, and thence to the rotation knob 90. Still referring to FIG. 1, if a tensioning mechanism 60 is mounted co-axial to the longitudinal axis A of the handle 10 and disposed within the handle 10 of the instrument, the axial portion of the tensioning mechanism 60 should provide a passage for the rod member 80. Thus, in the embodiment as shown in FIG. 1 in which the tensioning mechanism 60 has a screw member 64 disposed within the body of the handle 10 and mounted co-axial to the longitudinal axis A of the handle 10, the screw member 64 preferably has a screw bore 88 extending axially therethrough for the passage of the rod member 80.

The rod member 80 is preferably made of a flexible memory metal for allowing the recovery of the rod member's 80 initial, substantially linear shape, that is substantially co-axial to the longitudinal axis A of the handle 10 after the rod member 80 has been bent. This allows the rod member 80 to necessarily bend in response to the selective deflection of the articulating section 30 relative to the longitudinal axis A of the handle 10. The use of the flexible memory metal are preferably provides a spring force that acts on the articulating section 30 to provide a resistence to the movement of the articulating section 30.

The combination of the deflection tension applied to the flexible member 50 by the tensioning mechanism 60 and the spring force of the flexible memory metal rod member 80 allows for the precise positioning and holding of the articulating section 30 into the desired operative position. In the preferred embodiment, as shown in FIGS. 1, 4A and 4B, a gradual manipulation of the actuation nut 62 causes the axial translation of the screw member 64 within the sleeve bore 18 of the handle 10. As noted above, this axial translation imparts tension to the connected flexible member 50 which is transmitted to the portion of the flexible member 50 connected to the distal end 34 of the articulating section 30, thereby permitting the entire length of the controllably bendable articulating section 30 to be selectively deflected in the angular plane passing through the longitudinal axis A of the handle 10 at a controlled rate to the desired operative position. As the articulating section 30 is selectively deflected under the tension imparted to the flexible member 50, the flexible rod member 80 is placed under a bending load which causes the rod member 80 to act on the articulating section 30 to attempt to counter-act the applied tension and to attempt to pivotally rotate the articulating section 30 back to its fully-extended position.

The tension imparted by the axial translation of the, screw member 64 into the flexible member 50 and the counter-acting bending load of the flexible memory metal rod member 80 provides two distinct advantages. First, the articulating section 30 is stabilized and held in the desired operative position due to the bending load of the flexible rod member 80 acting on the articulating section 30 balancing against the tension applied by the flexible member 50 acting on the articulating section 30. Second, the spring force of the bending load of the flexible rod member 80 forces the actuation nut 62 into close cooperation with the sleeve bore 18 of the handle 10 which acts as a frictional clutch 74 that helps to prevent undesired movement of the actuation nut 62 and thus acts to help prevent unnecessary movement of the articulating section 30 when the desired operative position of the articulating section 30 is obtained. When it is desired to return the articulating section 30 to the fully-extended position the bending means is relaxed. When the tension in the flexible member 50 is released, there is no tension force applied to the flexible member 50 so that the spring force of the flexible rod member 80 will attempt to return rod member 80 to its original shape substantially co-axial to the longitudinal axis A of the handle 10, thereby also returning the articulating section 30 to its fully-extended position.

In one preferred embodiment, the rod member 80 comprises a length of flexible memory metal 96 and a length of non-flexible metal 98. The length of flexible memory metal 96 of the rod member 80 of this embodiment is disposed within and proximate the articulating section 30 so that the instrument 5 has the flexibility and spring force capability of the memory metal where desired. The length of flexible memory metal 96 is fixedly connected to the length of non-flexible metal 98 at a point intermediate the forward end 82 and back end 84 of the rod member 80. The flexible memory metal and non-flexible metal lengths 96, 98 may be connected by welding or crimping or by mechanical or chemical method that would be commonly used by one skilled in the art. It is also preferred that the flexible memory metal of the present invention be formed of Nitinol.

As shown in FIG. 1, a tubular flush port 110 may be provided for allowing fluid communication with the interior of the rigid tube section 20 and the articulating section 30 for cleansing. This flush port 110 may have a hollow male thread 112 extending from the bottom 111 of the flush port 110 that may act to secure the rigid tube section 20 to the front end 12 of the handle 10. The front end 12 of the handle 10 has a handle aperture 11 that has a threaded bore 13 sized to receive the hollow male thread 112 of the flush port 110. The rigid tube section 20 also has a tube aperture 24 that aligns with the handle aperture 11. When the tube aperture 24 is aligned with the handle aperture 11, the male thread 112 is threaded into the handle aperture 11 and extends into the tube aperture 24, thus fixating the rigid section 20 to the handle 10. The hollow characteristic of the tubular flush port 110 also provides for the cleansing of the interior of the rigid tube section 20 and the articulating section 30 by allowing the introduction of a cleansing liquid into the flush port 110 which is in fluid communication with the articulating bore 36 and the tube bore 22, thus allow surgical debris to be flushed out of the articulating section 30 and the rigid tube section 20. The cleansing capacity is enhanced if the articulating section 30 has the plurality of interengaging segments 38. The angular gaps in the articulating section 30 formed by the interengaging segments 38 are in fluid communication with the articulating bore 36 and therefore have the added benefit of allowing for the exit of surgical debris and cleansing fluid that is introduced into the flush port 110.

The present invention is ideally suited for use in heart surgery, in either open heart surgery or by minimally invasive endoscopic surgery, e.g., prosthetic heart valve implantation. For minimally invasive surgery, access to the heart may be achieved through the ribs of the patient using a rib spreader to provide an access port to the thoracic cavity. In the typical procedure, the surgeon will usually access the heart via the fourth intercostal space located between the third and fourth ribs, but this may be changed based on the individual patient's anatomy. In use, a prosthetic implant, such as a heart valve, is removably secured onto the complementary exterior surface 106 of the implant adaptor 100. The implant adaptor 100, the articulating section 30, in the fully-extended position, and a portion of the rigid tube section 20 is then inserted through the access port into the surgical site within the patient's body. The handle 10 of the instrument 5 is subsequently rotated so that the desired implantation site is within the angular plane of the articulating section 30. The bending means is then manipulated to bring the implant adaptor 100 into the desired operative position. If needed, refinements to the angular plane of the articulating section 30 may be made through further rotational manipulation of the handle 10. When the implant adaptor 100 has been brought into the desired operative position, the articulation section is held in position which fixes the angular position of the implant adaptor 100 in the angular plane relative to the longitudinal axis A of the handle 10. The rotation means is then manipulated to rotate the implant adaptor 100 so that the attached implant is brought into the desired anatomical orientation at the predetermined surgical site.

When the implant has been secured to the predetermined surgical site, the implant adaptor 100 is separated from the implant. If the implant is threadably attached to the implant adaptor 100, the rotation means is manipulated to back the male threaded post 101 of the implant adaptor 100 from the complementarily threaded implant. If the implant has a complementary surface structure, such as a female bayonet fitting, the instrument 5 is simply drawn gently back toward the access port until the complementarily exterior surface 106 of the implant adaptor 100 separates from the implant.

As can be appreciated, the instrument 5 of the present invention can be used in a reverse manner to secure to and remove previously implanted prosthesis. Further it can be appreciated that the instrument 5 of the present invention can be used in surgical procedures other than endoscopic heart valve surgery, including, for example, orthopedic procedures, general laproscopic procedures, gynecological procedures, plastic surgery procedures, and the like.

Although the present invention has been described with reference to specific details of certain embodiments thereof, it is not intended that such details should be regarded as limitations upon the scope of the invention except as and to the extent that they are included in the accompanying claims.

What is claimed is:

1. A surgical instrument for use in the body of a patient comprising:
    a handle having a front end and defining a longitudinal axis;
    an actuation member associated with the handle;
    an elongated tube section, extending longitudinally from the front end of said handle;
    an elongated tubular articulating section having a proximal end and an opposed distal end, the proximal end of said articulating section connected to the tube section;
    said actuation member being movable relative to the handle member for effecting pivotal movement of said articulating section from a fully extended position, wherein the articulating section is co-axial to the longitudinal axis of the handle, to a plurality of operative positions in response to movement of the actuation member, wherein said articulating section is selectively deflected in an angular plane passing through the longitudinal axis of said handle within a desired angular range of motion;
    a tool adaptor having a top end and a bottom end, the bottom end of said tool adaptor freely rotatable about the distal end of said articulating section; and
    a rotation member for effecting rotational movement of said tool adaptor relative to the distal end of said articulating section;
    wherein said tool adaptor may be oriented relative to the longitudinal axis of said handle by the bending of said articulating section and wherein said tool adaptor may be rotationally oriented relative to the distal end of said articulating section so that said tool adaptor may be articulated into a desired orientation within a body of a patient.

2. The instrument of claim 1, wherein said actuation member further includes:
    a flexible member extending longitudinally within the articulating section and connected near the distal end of the articulating section; and
    a tensioning mechanism operatively connected to said flexible member, wherein the tensioning mechanism may selectively apply tension to said flexible member to cause axial movement of said flexible member, thereby causing the articulating section to bend in response to movement of the actuation member.

3. The instrument of claim 2, wherein said tensioning mechanism comprises:
    a actuation nut movably mounted relative to the longitudinal axis of said handle; and
    an elongated screw member threadably adapted to be connected to said flexible member, wherein said screw member is movable relative to the longitudinal axis of said handle in response to movement of said actuation nut.

4. The instrument of claim 1, wherein said rotation comprises:
    an elongated rod member, having a forward end and an opposed back end, the forward end of said rod member fixedly attached to the bottom end of said tool adaptor, said rod member extending within said articulating section and said tube section; and
    a rotation knob rotationally mounted relative to the longitudinal axis of said handle, said rotation knob being operatively attached to said rod member so that said tool adaptor may be selectively rotated relative to the distal end of said articulating section upon rotation of said rotation knob.

5. The instrument of claim 4, wherein said rod member is comprised of a length of flexible memory metal and a length of non-flexible, metal, said length of flexible memory metal being disposed, within and proximate said articulating section proximate the forward end of said rod member, said length of flexible memory metal further being fixedly coupled to said length of non-flexible metal intermediate the forward end and the back end of said rod member, whereby said length of flexible memory metal bends in response to the movement of said actuation member and resultantly acts on said articulating section so that said articulating section will pivotally rotate toward the fully extended position of said articulating section upon relaxation of said bending means.

6. A surgical apparatus as in claim 4, wherein said rod member is comprised of a flexible memory metal.

7. The instrument of claim 1, wherein the desired angular range of motion of said articulating section is between 0 and 90 degrees.

8. The instrument of claim 1, wherein the articulating section comprises a plurality of interengaging segments co-axially aligned with each other and wherein said segments are pivotally moveable relative to each other.

9. The instrument of claim 1, wherein said articulating section has an outer surface and wherein the bottom end of said tool adaptor defines an internal bore with an inside diameter sized to freely overlap the outer surface of the distal end of said articulating section.

10. The instrument of claim 1, wherein said tool adaptor has an exterior surface shaped to removably engage a complementarily surfaced implant in the body of a patient.

11. The instrument of claim 1, wherein said tool adaptor has a male threaded post adapted to removably engage a complementarily threaded prosthetic device, in the body of a patient said post extending from the end of said tool adaptor.

12. The instrument of claim 1, wherein said tool adaptor has an exterior surface defining a male bayonet fitting adapted to removably engage a complementarily female bayonet fitted prosthetic device in the body of a patient, said male bayonet fitting extending from the exterior surface of said tool adaptor.

13. A surgical instrument for use in the body of a patient comprising:
    a handle having a longitudinal axis and a front end;

an actuation member associated with the handle;

an elongated tube section, having a tube bore therethrough, extending longitudinally from the front end of said handle;

a tubular elongated articulating section having an articulating bore therethrough, a proximal end, and an opposed distal end, the proximal end of said articulating section connected to the tube section;

a flexible member connected near the distal end of said articulating section wherein said articulating section is bendable upon the movement of said flexible member from a fully-extended position, wherein said articulating section is substantially co-axial to said tube section, to a plurality of operative positions, wherein said articulating section is selectively deflected in an angular plane passing through the longitudinal axis of said handle within a desired angular range of motion in response to movement of the actuation member and flexible member relative to the handle;

a tool adaptor having a top end and a bottom end; and a rotatable elongated rod member extending within the articulating bore and the tube bore, having a forward end, an opposed back end, the forward end of said rod member connected to the bottom end of said tool adaptor, wherein said tool adaptor may be selectively rotated about the distal end of said articulating section upon the rotational movement of said rod member;

wherein said tool adaptor may be oriented relative to the longitudinal axis of said handle by the bending of said articulating section and wherein said tool adaptor may be rotationally oriented relative to the distal end of said articulating section so that the tool adaptor may be articulated into a desired orientation within a surgical field within a body of a patient.

14. The instrument of claim 13, wherein said articulating section includes a plurality of interengaging segments and wherein said segments are pivotally moveable relative to each other in response to movement of the actuation member relative to the handle.

15. The instrument of claim 13, wherein the actuation member further includes:

an actuation nut mounted relative to the longitudinal axis of said handle; and an elongated screw member adapted to be connected to said flexible member, wherein said screw member is movable in an axial direction relative to the longitudinal axis of said handle in response to movement of said actuation nut.

16. The instrument of claim 13, further comprising a rotation knob rotationally mounted relative to the longitudinal axis of said handle, said rotation knob connected to the said rod member such that said rod member is rotationally movable in response to rotation of said rotation knob.

17. The instrument of claim 13, wherein said rod member is comprised of a length of flexible memory metal whereby said length of flexible memory metal bends in response to the movement of said actuation member and resultantly acts on said articulating section so that said articulating section will pivotally rotate toward the fully extended position of said articulating section upon relaxation of tension in said flexible member.

18. A surgical instrument as in claim 13, wherein said articulating section includes a rod member that is comprised of a flexible memory metal.

19. The instrument of claim 13, wherein the desired angular range of motion of said articulating section is between 0 and 90 degree.

20. The instrument of claim 13, further comprising a flush port associated with the tube section and in fluid communication with said tube bore and said articulating section bore.

21. The instrument of claim 13, wherein said articulating section has an outer surface and wherein the bottom end of said tool adaptor defines an internal bore with an inside diameter sized to freely overlap the outer surface of the distal end of said articulating section.

22. The instrument of claim 13, wherein said tool adaptor has an exterior surface shaped to removably engage a complementarily surfaced implant in the body of a patient.

23. The instrument of claim 13, wherein said tool adaptor has a male threaded post adapted to removably engage a complementarily threaded prosthetic device in the body of a patient.

24. The instrument of claim 13, wherein said tool adaptor has an exterior surface defining a fitting adapted to removably engage a complementarily fitted implantable prosthetic device, said fitting extending from the exterior surface of said tool adaptor.

25. A surgical instrument for use in the body of a patient comprising:

a handle having a front end and defining a longitudinal axis;

an actuation member associated with the handle;

an elongated section having at least a portion thereof forming an articulating section;

said actuation member being movable relative to the handle member for effecting pivotal movement of said articulating section from a fully extended position, wherein the articulating section is generally co-axial with the longitudinal axis of the handle, to a plurality of operative positions in response to movement of the actuation member relative to the handle member, wherein said articulating section is selectively deflected in an angular plane passing through the longitudinal axis of said handle within a desired angular range of motion;

a tool adaptor having an end thereon adapted to engage an implant for use in the body of a patient and wherein said tool adaptor is freely rotatable about the distal end of said articulating section; and a rotation member for effecting rotational movement of said tool adaptor relative to the distal end of said articulating section;

wherein said tool adaptor may be oriented relative to the longitudinal axis of said handle by the bending of said articulating section and wherein said tool adaptor may be rotationally oriented relative to the distal end of said articulating section so that said tool adaptor may be articulated into a desired orientation within the body of a patient.

26. The surgical instrument of claim 25 wherein said tool adaptor is independently rotational with respect to said articulating section irrespective of the orientation of the articulating section relative to the longitudinal axis of the handle.

27. The surgical instrument of claim 25 wherein movement of said actuation member relative to said handle causes a plurality of interengaging segments to pivotally move relative to each other.

28. The surgical instrument of claim 25 wherein the elongated section includes an elongate rod member extending therethrough and movement of said actuation member relative to said handle causes the elongate member to move relative to the elongated section.

29. The surgical instrument of claim 28 wherein the rod member is movable relative to the tool adaptor in response to movement of the actuation member relative to the handle.

30. The surgical instrument of claim 28 wherein movement of the actuation member relative to the handle causes the rod member to move relative to the tool adaptor and effects pivotal movement of the articulating section.

31. The surgical instrument of claim 28 wherein at least a portion of the rod member is formed of a flexible memory metal.

32. The surgical instrument of claim 25 the desired angular range of motion of the articulating section is between 0 and 90 degrees relative to the longitudinal axis of the handle.

33. A method of using a surgical instrument in surgery for implantation of a prosthetic implant device, the method including the steps of;

providing a surgical instrument for use in the body of a patient having a handle having a front end and defining a longitudinal axis withan actuation member associated with the handle and an elongated section having at least a portion thereof forming an articulating section and further including a tool adaptor having an end thereon adapted to engage an implant for use in the body of a patient and wherein said tool adaptor is freely rotatable about the distal end of said articulating section and a rotation member for effecting rotational movement of said tool adaptor relative to the distal end of said articulating section;

causing the movement of the actuation member relative to the handle member for effecting pivotal movement of said articulating section from a fully extended position, wherein the articulating section is generally co-axial with the longitudinal axis of the handle, to a plurality of operative positions in response to movement of the actuation member relative to the handle member, wherein said articulating section is selectively deflected in an angular plane passing through the longitudinal axis of said handle within a desired angular range of motion;

orienting the tool adaptor relative to the desired location in a surgical field and longitudinal axis of the handle by the bending of the articulating section in response to the movement of the actuation member relative to the handle; and rotationally adjusting the tool adaptor relative to the distal end of said articulating section and the desired location in the surgical field so that said tool adaptor may be articulated into a desired orientation within the body of a patient to perform a procedure with a prosthetic implant.

* * * * *